United States Patent [19]

Partridge et al.

[11] Patent Number: 5,296,481
[45] Date of Patent: Mar. 22, 1994

[54] TREATMENT PROCESS FOR PROMOTING WEIGHT LOSS EMPLOYING A SUBSTITUTED Δ5-ANDROSTENE

[75] Inventors: Bruce E. Partridge, Lincoln, Nebr.; Henry A. Lardy, Madison, Wis.

[73] Assignee: Humanetics Corporation, Chaska, Minn.

[21] Appl. No.: 867,288

[22] Filed: Apr. 10, 1992

Related U.S. Application Data

[63] Continuation of Ser. No. 575,156, Aug. 29, 1990, abandoned.

[51] Int. Cl.⁵ .......................... A61K 31/56; C07J 1/00
[52] U.S. Cl. .................................... 514/178; 514/177; 514/182; 552/615; 552/621; 552/622
[58] Field of Search ............... 514/169, 177, 128, 182; 552/619, 620, 622, 502

[56] References Cited

U.S. PATENT DOCUMENTS

| | | | |
|---|---|---|---|
| 4,511,511 | 4/1985 | Lewbart | 260/239.55 |
| 4,518,595 | 5/1985 | Coleman et al. | 514/178 |
| 4,666,888 | 5/1987 | Coleman et al. | 514/177 |
| 4,897,390 | 1/1990 | Ruhe | 514/177 |
| 4,898,694 | 2/1990 | Schwartz et al. | 260/397.5 |

*Primary Examiner*—Frederick E. Waddell
*Assistant Examiner*—T. J. Criares
*Attorney, Agent, or Firm*—Faegre & Benson

[57] ABSTRACT

A method for controlling weight gain or promoting weight loss which includes the step of treating a subject with an effective weight gain controlling or weight loss promoting amount of a substituted Δ5-Androstene which is biologically effective for controlling weight gain or promoting weight loss and biologically ineffective for promoting the synthesis of sex hormones. Steroids believed to provide the desired weight control/weight loss characteristics include:

Δ5-Androstene-3β,7α-diol-17-one
Δ5-Androstene-3β-ol-7,17-dione
Δ5-Androstene-3β,7α,17-triol
Δ5-Androstene-3β,17β-diol-7-one and various derivatives thereof.

17 Claims, No Drawings

TREATMENT PROCESS FOR PROMOTING WEIGHT LOSS EMPLOYING A SUBSTITUTED Δ5-ANDROSTENE

This is a continuation of application Ser. No. 07/575,156, filed 29 Aug. 1990 now abandoned.

FIELD OF THE INVENTION

Broadly, the invention relates to the use of steroids for effecting a desired biological response. Specifically, the invention relates to the use of a substituted dehydroepiandrosterone capable of effecting a variety of beneficial biological responses without inducing the formation of androgen and estrogen hormones which is commonly associated with dehydroepiandrosterone treatment.

BACKGROUND

Dehydroepiandrosterone (Δ5-androstene 3β-hydroxy, 17-one) (hereinafter referenced as DHEA) is a natural steroid produced in the adrenal glands, testes and brain. Dehydroepiandrosterone is an intermediate in the biosynthetic production of estrogen and androgen (sex hormones) from 17α-hydroxy pregnenolone.

Treatment with DHEA is believed to stimulate various biological responses including promoting weight loss and inducing an increase in the production of the sex hormones androgen and estrogen.

The ability of DHEA to promote weight control is believed to be mediated through enhanced thermogenesis (conversion to heat energy rather than chemical energy such as ATP and/or triacylglycerides). The thermogenic effect of DHEA is believed to result from a stimulation in the synthesis of liver thermogenic enzymes such as mitochondrial glycerol 3-phosphate dehydrogenase (G3P-DH) and cytosolic malic enzyme (ME) which tend to reduce the efficiency of energy metabolism.

Unfortunately, DHEA is not useful as a therapeutic agent for controlling weight gain/promoting weight loss because the dose rate of DHEA necessary to achieve these desired characteristics may also stimulate the production of sex hormones which is associated with various undesired side effects.

Accordingly, a therapeutic agent possessing the weight loss characteristic of DHEA without the associated sex hormone stimulating characteristic would be extremely useful.

SUMMARY OF THE INVENTION

A method for controlling weight gain and/or promoting weight loss which includes the step of treating a weight loss promoting amount of a substituted Δ5-Androstene effective for stimulating the desired biological response while ineffective for inducing the synthesis of sex hormones.

Steroids believed to provide the desired beneficial biological results include:
Δ5-Androstene-3β,7α-diol-17-one
Δ5-Androstene-3β-ol-7,17-dione
Δ5-Androstene-3β,7α,17-triol
Δ5-Androstene-3β,17β-diol-7-one
and derivatives thereof wherein (i) at least one of the hydroxyl groups is esterified with an acid
selected from the group consisting of (i) $C_{2-22}$ aliphatic acids that may or may not contain one or more double bonds and may or may not contain branched carbon chains, (ii) $C_{7-12}$ aromatic acids, (iii) $C_3$ or larger dicarboxylic acids in which only one of the carboxyl groups is esterified to the hydroxyl group(s) on the steroid leaving the second carboxyl group free or in the form of a salt, or (iv) inorganic acids such as sulfuric and phosphoric.

These steroids may also be administered as carbamates, enanthates and other derivatives capable of releasing the free steroid in the intestinal tract, the blood or in tissues. The desired biological activity is a function of the steroid moiety. Derivation of the moiety may serve a variety of possible functions including stabilization of the steroid, flavoring or obscuring the natural flavor of the steroid, or affecting the rate of absorption of the steroid.

DETAILED DESCRIPTION OF THE INVENTION INCLUDING A BEST MODE

Δ5-Androstenes substituted at C-3, C-7 and/or C-17 with a hydroxyl or keto group are biologically effective for controlling weight gain and promoting weight loss without substantial stimulation in the production of sex hormones. Derivatives of these substituted Δ5-Androstenes in which at least one of the hydroxyl groups is esterified with an acid selected from the group consisting of (i) $C_{2-22}$ aliphatic acids that may or may not contain one or more double bonds and may or may not contain branched carbon chains, (ii) $C_{7-12}$ aromatic acids, (iii) $C_3$ or larger dicarboxylic acids in which only one of the carboxyl groups is esterified to the hydroxyl group(s) on the steroid leaving the second carboxyl group free or in the form of a salt, or (iv) inorganic acids such as sulfuric and phosphoric, are also believed to possess the desired characteristics.

These steroids may also be administered as carbamates, enanthates and other derivatives capable of releasing the free steroid in the intestinal tract, the blood or in tissues. The desired biological activity is a function of the steroid moiety; the derivatizing moiety may serve to stabilize the steroid, to favor or to retard absorption or to obscure its flavor.

SYNTHESIS

Δ5-Androstene 3β,7-diol, 17-one (7-hydroxy DHEA)

Δ5-Androstene 3β,7α-diol, 17-one (7-hydroxy DHEA) can be synthesized from commercially available DHEA acetate by sequentially synthesizing:

Δ5-androstene 3β-hydroxy-17-one acetate
Δ5-androstene 3β-hydroxy-7-bromo-17-one
Δ5-androstene 3β,7α-hydroxy-17-one diacetate
Δ5-androstene 3β,7α-hydroxy-17-one Δ5-androstene 3β-hydroxy-7-bromo-17-one (7-bromo DHEA) can be synthesized from Δ5-androstene 3β-hydroxy-17-one acetate (DHEA acetate) by reacting the DHEA acetate with a brominating agent such as Dibromantin (1,3 dibromo 5,5 dimethylhydantoin) or N-bromo succinimide. 7-bromo DHEA is unstable and must be used immediately in the next step of the process.

The 7-bromo DHEA containing an isomeric mixture of 7α-bromo DHEA and 7β-bromo DHEA may be equilibrated to 7α-bromo DHEA in accordance with the method described for a cholesterol derivative in Confalone, P. N., Kulesha, I. D., and Uskokovic, M. R. *Jour. Org. Chem.*, vol. 46, pp 1030–1032 (1981). Briefly the racemic mixture of 7-bromo DHEA is contacted with cold anhydrous LiBr and shielded from light until the stereospecific composition is achieved.

Δ5-androstene 3β,7-hydroxy-17-one diacetate (7-hydroxy DHEA diacetate) may be synthesized from the 7-bromo DHEA by reacting the 7-bromo DHEA with a mixture of glacial acetic acid and powdered silver acetate at room temperature in a suitable solvent such as methylene chloride or acetone.

Δ5-androstene 3β,7α-hydroxy, 17-one (7-hydroxy DHEA)2 may be synthesized from the 7-hydroxy DHEA diacetate by reacting the 7-hydroxy DHEA diacetate dissolved in methanol with an aqueous solution containing a suitable base such as Na₂CO₃.

The synthesized 7-hydroxy DHEA may then be purified by (i) evaporating the methanol in vacuo, (ii) extracting the 7-hydroxy DHEA into an appropriate organic solvent such as dichloromethane, (iii) evaporating the organic solvent in vacuo, (iv) azeotropically drying the extracted solids containing the 7-hydroxy DHEA with a suitable organic solvent such as ethanol, (v) dissolving the extracted solids in acetone, and then (vi) adding a suitable precipitating agent, such as hexane, to the acetone solution to produce purified crystals of Δ5-Androstene 3β,7α-diol, 17-one.

A second crop of Δ5-Androstene 3β,7α-diol, 17-one crystals may be obtained by cooling the resultant solution below room temperature.

Δ5-Androstene-3β-ol 7,17-dione (7-keto DHEA)

Δ5-Androstene 3β-ol, 7,17-dione can be synthesized from commercially available DHEA acetate by sequentially synthesizing:
3β-acetoxy-Δ5-androstene-17-one
3β-acetoxy-{5-androstene-7,17-one
Δ5-androstene 3β-hydroxy-7,17-one 3β-acetoxy-Δ5-androstene-7,17-one (7-one DHEA acetate) can be synthesized from 3β-acetoxy-Δ5-androstene-17-one (DHEA acetate) by reacting the DHEA acetate with the oxidizing agent CrO₃ in accordance with the procedure outlined in Fieser, L. F., *Jour. Am. Chem. Soc.*, vol. 75, pp 4386–4394 (1953).

Δ5-androstene 3β-hydroxy-7,17-dione (7-one DHEA) can be synthesized from the 7-one acetate and purified by employing the deesterification and purification steps set forth above with respect to the synthesis and purification of 7-hydroxy DHEA from 7-hydroxy DHEA diacetate.

Δ5-Androstene 3β,7α,17β-triol (7α-hydroxy Androstenediol)

Δ5-Androstene 3β,7α,17β-triol can be synthesized from commercially available Androstenediol diacetate by sequentially synthesizing:
Δ5-androstene 3β,17β-diol, diacetate
Δ5-androstene 3β,17β-diol-7-bromide diacetate
Δ5-androstene 3β,7α,17β-triol-3,17-diacetate
Δ5-androstene 3β,7α,17β-triol Δ5-androstene 3β,17β-diol-7-bromide (7-bromo Androstenediol) can be synthesized from the commercially available Δ5-androstene 3β,17β-diol diacetate (Androstenediol diacetate) by reacting the Androstenediol diacetate with a brominating agent such as Dibromantin (1,3 dibromo 5,5 dimethylhydantion) or N-bromosuccinimide. The synthesized 7-bromo Androstenediol is unstable and must be used immediately.

The 7-bromo Androstenediol contains an isomeric mixture of 7α-bromo Androstenediol and 7β-bromo Androstenediol which can be equilibrated to 7α-bromo Androstenediol in accordance with the method described in Confalone, P. N., Kulesha, I. D., and Uskokovic, M. R. *Jour. Org. Chem.*, vol. 46, pp 1030–1032 (1981). Briefly the racemic mixture of 7-bromo Androstenediol is contacted with anhydrous LiBr and shielded from light until the stereospecific composition is achieved.

Δ5-androstene 3β,7α,17β-triol-3,17-diacetate (7-hydroxy Androstenediol diacetate) may be synthesized from the 7-bromo Androstenediol by reacting the 7-bromo Androstenediol with a mixture of glacial acetic acid and silver acetate in a suitable solvent such as methylene chloride or acetone.

Δ5-androstene 3β,7α,17β-triol (7-hydroxy Androstenediol) may be synthesized from the 7-hydroxy Androstenediol diacetate by reacting the 7-hydroxy Androstenediol diacetate in methanol with an aqueous solution containing a suitable base such as Na₂CO₃.

The synthesized 7-hydroxy Androstenediol may then be purified by (i) evaporating the methanol in vacuo, (ii) extracting the 7-hydroxy Androstenediol into an appropriate organic solvent such as dichloromethane, (iii) evaporating the organic solvent in vacuo, (iv) azeotropically drying the extracted solids containing the 7-hydroxy Androstenediol with a suitable organic solvent such as ethanol, (v) dissolving the extracted solids in acetone, and then (vi) adding a suitable precipitating agent, such as hexane, to the acetone solution to produce purified crystals of Δ5-Androstene 3β,7α,17β-triol.

A second crop of Δ5-Androstene 3β,7α,17β-triol crystals may be obtained by cooling the resultant solution below room temperature.

Δ5-Androstene 3β,17β diol, 7-one (7-keto Androstenediol)

Δ5-Androstene 3β,17β-diol-7-one can be synthesized from commercially available androstenediol diacetate by sequentially synthesizing:
Δ5-androstene 3β,17β-diol diacetate
Δ5-androstene 3β,17β-diol-7-one diacetate
Δ5-androstene 3β,17β-diol-7-one Δ5-androstene 3β,17β-diol-7-one diacetate can be synthesized from Δ5-androstene 3β,17β-diol diacetate (Androstenediol diacetate) by reacting the androstenediol diacetate with the oxidizing agent CrO₃ in accordance with the procedure outlined in Fieser, L. F., *Jour. Am. Chem. Soc.*, vol. 75, pp 4386–4394 (1953).

Δ5-androstene 3β,17β-diol-7-one (7-one androstenediol) can be synthesized from the Δ5-androstene 3β,17β-diol-7-one diacetate and purified by employing the deesterification and purification steps set forth above with respect t the synthesis and purification of 7-hydroxy DHEA from 7-hydroxy DHEA diacetate.

Without intending to be unduly limited thereby, it is believed that the substituted Δ5-Androstenes may be further modified by esterifying one or more of the hydroxyl groups with any of a variety of organic acids and inorganic acids such as sulfuric or phosphoric acid.

TREATMENT

A subject may be treated with the substituted Δ5-Androstenes by any of the commonly accepted practices including orally or by injection. It is believed that treatment at a dosage rate of about 0.1 to 2 grams, preferably about 0.5 to 2 grams, steroid per 100 kilograms body weight per day is generally effective for promoting weight loss and/or preventing weight gain. A dose rate of less than about 0.1 gram per 100 kilograms bodyweight is believed to be generally ineffective for preventing weight gain while a dose rate of greater than about 2 grams per 100 kilograms bodyweight increases the cost of treatment without providing a corresponding benefit in performance. The optimum dose rate to be administered to a subject is case specific as the optimum dose rate depends upon several factors including current body composition (percent fat), the desired effect (weight gain prevention versus weight loss), eating habits of the individual (daily caloric intake), and the like. As would be expected, the dose rate provided to a subject for the purpose of promoting weight loss will be greater than that necessary to promote weight maintenance assuming identical caloric intake under each program.

Without intending to be limited thereby, we believe that the substituted Δ5-Androstenes are metabolic intermediates between the conversion of DHEA to a metabolite(s) actually responsible for enhancing the production of thermogenic enzymes such as glycerol 3-phosphate dehydrogenase and malic enzyme.

The subject may be treated with a steroid on any desired schedule. It is anticipated that the steroid will be effective for preventing weight gain and/or promoting weight loss not only while actively present within the body, but also for as long as the concentration of the induced thermogenic enzyme(s) remain elevated. At the present time, the duration of effectiveness for the steroid is not fully appreciated. However, it is believed that the steroid is not stored within the body and will be substantially removed and/or deactivated within days after administration. Accordingly, the subject should be conveniently treated every day for optimum performance but may be treated less frequently such as every other day or every week when less than maximum performance is acceptable. For example, a subject placed on a weight maintenance program may require treatment with the steroid only once a week even though the steroid and the induced thermogenic enzyme(s) are not retained during the entire period between treatments as the weight loss occurring within the first few days after treatment counterbalances any weight gain occurring during the remaining days between treatments.

As is apparent from the factors which affect dosage and dose rate, each particular subject should be carefully and frequently reviewed and the dosage and/or dose rate altered in accordance with the particular situation.

EXPERIMENTAL

EXAMPLE I

Synthesis

Δ5-Androstene 3β,7α-diol-17-one (Step 1) Into a two liter, triple neck, round bottom, flask equipped with a magnetic stirrer and a reflux condenser was placed 1000 ml hexane (b.p 69°-71°), 10 grams (0.03 moles) DHEA acetate and 13.6 grams (0.16 moles) NaHCO$_3$ to form a first solution. The first solution was placed under a N$_2$ atmosphere and heated under constant agitation to reflux. Into the refluxing first solution was added 6.11 grams (0.021 moles) Dibromantin (1,3 dibromo 5,5 dimethylhydantion) as a brominating agent to form a second solution. The second solution gradually turned orange after which it rapidly turned a pale white/light yellow. The second solution was refluxed for 30 minutes, cooled to room temperature and filtered through a sintered glass funnel. The residue was rinsed with 50 ml dichloromethane and the combined filtrate rotovapped to dryness at a temperature of less than 35° C. The dry filtrate (Δ5-Androstene 3β-ol-7-bromo-17-one) is unstable to storage and was used immediately in step two.

(Step 2) The dry filtrate was resolubilized in 80 ml of dichloromethane in a one liter stoppered flask equipped with a magnetic stirrer and placed in an ice bath. Into the resolubilized filtrate was added 8 grams anhydrous LiBr in 320 ml ice-cold acetone to form a third solution. The third solution was shielded from light and stirred continuously for three hours. The resulting solution of predominantly (Δ5-Androstene 3β-ol-7α-bromo-17-one) was allowed to warm briefly and used immediately in step three.

(Step 3) Into a 500 ml flask equipped with a magnetic stirrer was placed 320 ml dichloromethane, 80 ml glacial acetic acid, and 26 grams of silver acetate to form a first suspension. The first suspension was stirred continuously for 20 minutes at room temperature. The stirred first suspension was added under constant agitation into the warmed solution of predominantly Δ5-Androstene 3β-ol-7α-bromo-17-one to form a second suspension. The second suspension was constantly stirred for 30 minutes at room temperature during which the suspension gradually darkened. The darkened suspension was filtered through a sintered glass funnel to produce a solid fraction. The filtered solid fraction was rinsed with 100 ml dichloromethane. The filtrate was extracted three times with 1000 ml of water, neutralized with 1000 ml of a 5% NaHCO$_3$ solution, and extracted twice more with water. The organic solution containing the Δ5-Androstene 3β,17β-diol-17-one diacetate was then rotovapped to dryness.

(Step 4) The dried extracted solids were resolubilized in 500 ml methanol in a one liter, triple necked flask equipped with a magnetic stirrer and a reflux condenser to form a fourth solution. The fourth solution was placed under a N$_2$ atmosphere and heated under constant stirring to reflux. Into the fourth solution was added 250 ml of a 5% aqueous solution of Na$_2$CO$_3$ to form a fifth solution. The fifth solution was refluxed under constant agitation for 45 minutes. The methanol was rotovapped off and the aqueous fifth solution carefully brought to a pH of 7 with an appropriate amount of glacial acetic acid. The neutralized fifth solution was extracted twice with 100 ml of dichloromethane. The dichloromethane solution of Δ5-Androstene 3β,7α-diol-17-one was rotovapped to near dryness, azeotropically dried with absolute ethanol, and then azeotropically dried twice with acetone. Warm acetone was added to the dried extracted solids until the solids were completely dissolved to form a sixth solution. Hexane was added to the sixth solution until the solution began to cloud at which time crystals of Δ5-Androstene 3β,7α-diol-17-one began to form at room temperature.

A second crop of Δ5-Androstene 3β,7α-diol-17-one crystals was obtained by cooling the remaining sixth solution.

The product melts at about 187°-189° C. and when recrystallized from acetone/hexane melts at about 192°-193° C.

Example II

Synthesis

Δ5-Androstene 3β,7(α,β)-diol-17-one

Δ5-Androstene 3β,7(α,β)-diol-17-one was manufactured in accordance with the procedure set forth in Example I except that Step 2 was eliminated with the dried filtrated from Step 1 simply resolubilized in the 80 ml of dichloromethane in preparation for Step 3.

Example III

Synthesis

Δ5-Androstene-3β-ol-7,17-dione (Step 1) Into a 50 ml flask equipped with a magnetic stirrer and a water bath was placed 6.5 ml acetic anhydride, 23 ml acetic acid, 1.7 grams sodium acetate, and 2 grams DHEA acetate to form a first mixture. Into the first mixture was added 2 grams chromium trioxide over a thirty minute period to form a second mixture. The first mixture was maintained at a constant temperature of 56°-58° C. and continuously agitated during addition of the chromium trioxide. The second mixture was maintained at 56°-58° C. and continuously agitated for an additional hour after which the second mixture was cooled and slowly poured under continuous agitation into 600 ml of ice water to form a precipitate. The flocculent precipitate was collected on a sintered glass funnel and washed with water until no longer green. After drying in vacuo over $P_2O_5$ the product was dissolved in methanol and then recrystallized to yield substantially pure Δ5-Androstene 3β-acetoxy-7,17-dione having a melting point of about 191°-192° C.

(Step 2) The precipitate was resolubilized in 500 ml of methanol in a one liter, triple necked, round bottom flask equipped with a magnetic stirrer and a reflux condenser to form a third solution. The third solution was placed under a $N_2$ atmosphere and heated under constant agitation to reflux. Into the third solution was added 250 ml of a 5% aqueous solution of $Na_2CO_3$ to form a fourth solution. The fourth solution was refluxed under constant agitation for 45 minutes. The methanol was rotovapped off and the aqueous fourth solution carefully brought to a pH of 7 with an appropriate amount of glacial acetic acid. The neutralized fourth solution was extracted with two 100 ml portions of dichloromethane, the two portions combined, and the dichloromethane evaporated in vacuo. The extracted solids were then azeotropically dried first with absolute ethanol and then with two separate portions of acetone. Methanol was added to the dried extracted solids until the solids were completely dissolved to form a fifth solution. Hexane was added to the fifth solution until the solution began to cloud at which time crystals of Δ5-Androstene-3β-ol-7,17-dione began to form at room temperature.

A second crop of Δ5-Androstene-3β-ol-7,17-dione crystals was obtained by cooling the remaining sixth solution.

The resultant product had a melting point of about 35°-238° C.

Example IV

Synthesis

Δ5-Androstene 3β,7,17-triol (Step 1) Into a two liter round bottom flask equipped with a magnetic stirrer and a reflux condenser was placed 1000 ml hexane (b.p 69°-71°), 10 grams (0.03 moles) Δ5-Androstene-3β,17β-diol diacetate and 13.6 grams (0.16 moles) $NaHCO_3$ to form a first solution. The first solution was placed under a $N_2$ atmosphere and heated under constant agitation to reflux. Into the refluxing first solution was added 6.11 g (0.021 moles) Dibromantin (1,3-dibromo-5,5-dimethylhydantion) as a brominating agent to form a second solution. The second solution gradually turned orange after which it rapidly turned a pale white/light yellow. The second solution was refluxed for 30 minutes, cooled to room temperature and filtered through a sintered glass funnel. The residue was rinsed with 50 ml dichloromethane and the filtrates rotovapped to dryness at a temperature of less than 35° C. The dry filtrate (Δ5-Androstene-3β,17-diol-7-bromide) is unstable to storage and was used immediately in step two.

(Step 2) The dried filtrate was resolubilized in 80 ml of dichloromethane in a flask equipped with a magnetic stirrer and placed in an ice bath. Into the resolubilized filtrate was added 8 g anhydrous LiBr in 320 ml ice-cold acetone to form a third solution. The third solution was shielded from light and stirred continuously for three hours. The resulting solution of predominantly Δ5-Androstene-3β,17β-diol-7α-bromide was allowed to warm briefly and used immediately.

(Step 3) Into a 500 ml flask equipped with a magnetic stirrer was placed 320 ml methylene chloride, 80 ml glacial acetic acid, and 26 grams silver acetate to form a first suspension. The first suspension was stirred continuously for 20 minutes at room temperature. The stirred first suspension was added under constant agitation to the warmed solution of predominantly Δ5-Androstene-3β,17-diol-7α-bromide to form a second suspension. The second suspension was constantly stirred for 30 minutes at room temperature during which the suspension gradually darkened and was then filtered through a sintered glass funnel. The residual solids retained on the glass filter were rinsed with 100 ml dichloromethane. The filtrate was extracted three times with 1000 ml of water, neutralized with 1000 ml of a 5% $NaHCO_3$ solution, and then extracted twice more with water. The solids extracted from the filtrate (Δ5-Androstene-3β,7α,17β-triol-3,17-diacetate) were rotovapped to dryness.

(Step 4) The dried extracted solids were resolubilized in 500 ml methanol contained in a one liter, triple necked, round bottom flask equipped with a magnetic stirrer and a reflux condenser to form a fourth solution. The fourth solution was placed under a $N_2$ atmosphere and heated under constant agitation to reflux. Into the fourth solution was added 250 ml of a 5% aqueous solution of $Na_2CO_3$ to form a fifth solution. The fifth solution was refluxed under constant agitation for 45 minutes. The methanol was rotovapped off and the aqueous fifth solution carefully brought to a pH of 7 with an appropriate amount of glacial acetic acid. The neutralized fifth solution was extracted twice with 100 ml dichloromethane and the combined extract evaporated in vacuo. The extracted solids (Δ5-Androstene-3β,7α,17β-triol) were azeotropically dried with absolute ethanol and then twice with acetone. Warm acetone was added to the dried extracted solids until the solids were completely dissolved to form a sixth solution. Hexane was added to the sixth solution until the solution began to cloud at which time crystals of Δ5-

Androstene-3β,7α,17β-triol began to form at room temperature.

A second crop of Δ5-Androstene-3β,7α,17β-triol crystals was obtained by cooling the remaining sixth solution.

Example V

Synthesis

Δ5-Androstene-3β,7(α,β),17-triol

Δ5-Androstene-3β,7(α,β),17-triol was manufactured in accordance with the procedure set forth in Example III except that Step 2 was eliminated and the dried filtrated material from Step 1 was simply resolubilized in 80 ml of methylene chloride in preparation for Step 3.

Example VI

Synthesis

Δ5-Androstene-3β,17β-diol-7-one (Step 1) Into a 50 ml flask equipped with a magnetic stirrer and a water bath was placed 6.5 ml acetic anhydride, 23 ml acetic acid, 1.7 grams sodium acetate, and 2 grams androstenediol diacetate to form a first mixture. Into the first mixture was added 2 grams chromium trioxide over a thirty minute period to form a second mixture. The first mixture was maintained at a constant temperature of 56°-58° C. and continuously agitated during addition of the chromium trioxide. The second mixture was maintained at 56°-58° C. and continuously agitated for an additional hour after which the second mixture was cooled and slowly poured under continuous agitation into 600 ml of ice water to form a precipitate. The flocculent precipitate was filtered through a sintered glass funnel, washed with water until no longer green and dried in vacuo.

(Step 2) The dried precipitate was resolubilized in 500 ml of methanol contained in a one liter, round bottom flask equipped with a magnetic stirrer and a reflux condenser to form a third solution. The third solution was placed under a $N_2$ atmosphere and heated under constant agitation to reflux. Into the third solution was added 250 ml of a 5% aqueous solution of $Na_2CO_3$ to form a fourth solution. The fourth solution was refluxed under constant agitation for 45 minutes. The methanol was rotovapped off and the aqueous fourth solution carefully brought to a pH of 7 with an appropriate amount of glacial acetic acid. The neutralized fourth solution was extracted twice with 100 ml portions of dichloromethane and the combined extract evaporated in vacuo. The extracted solids were azeotropically dried with absolute ethanol and then twice with acetone. Methanol was added to the dried extracted solids until the solids were completely dissolved to form a fifth solution. Hexane was added to the fifth solution until the solution began to cloud at which time crystals of Δ5-Androstene-3β,17β-diol-7-one began to form at room temperature.

The resultant product had a melting point of about 200°-202° C.

Example VII

Enzymatic Activity Protocol

Administration of Hormone: Male Sprague Dawley rats weighing 125-150 gm were obtained from Sasco Inc. of Oregon, Wis. The rats were allowed free access to water and Purina Rat Chow pellets for the first day after arrival Administration of the steroids began on day two. The steroids were either administered orally (combined with the Purina Rat Chow) or injected intraperitoneal as set forth in Table 1 for 6 days.

Preparation of Liver Mitochondria and Cytosol. The treated rats were sacrificed by decapitation after 6 days of treatment. The livers were excised, placed in 10 ml of a buffer consisting of 250 mM mannitol, 70 mM sucrose, and 3 mM Hepes (hereinafter MSH buffer) at pH 7.4, weighed, removed from the buffer, minced with scissors, washed with MSH buffer, suspended in MSH buffer at a ratio of 1 gram minced liver to 5 ml MSH buffer, and homogenized with a Potter-Elvehjem rotary homogenizer.

The Mitochondria fraction was prepared by the method described in Johnson, D. and Lardy, H. A., *Methods Enzymology*, vol. 10, pp 94-96 (1967) which is hereby incorporated by reference. Briefly, liver homogenate was centrifuged in a Beckman Model J2-21 centrifuge, JA-20 rotor at 750 g for 10 minutes and the resulting supernatant solution centrifuged at 15,000 g for an additional 10 minutes. The resulting mitochondrial pellets were washed twice with MSH buffer, resuspended in 0.8 to 1 ml of a 35 wt % aqueous glycerol solution, and stored at $-70°$ C.

The Cytosolic fraction was obtained by recentrifuging the previously centrifuged supernatant solution at 100,000 g for 30 minutes in a Beckman Model L2 ultracentrifuge, type 40 rotor. The resultant supernatant solution was stored at $-70°$ C.

Protein concentrations in the resultant preparations were determined by the Biuret method described in Layne E., *Methods Enzymology*, vol. 3, pp 450451 (1957) which is hereby incorporated by reference. Briefly, the protein concentrations were determined by treating a dilute protein solution with copper tartrate solution and measuring the optical density at 540 nm.

Enzyme Assays. Mitochondrial G3P-DH activity was measured by the method described in Wernette, M. E., Ochs, R. S., and Lardy, H. A., *J. Biol. Chem.*, vol. 256, pp 12767-12771 (1981) which is a modified version of the method described in Gardner, R. S., Anal. Biochem., vol. 59, pp 272-276 (1974). Both references are hereby incorporated by reference. Briefly, aliquots of the previously prepared mitochondria containing 0.1 to 0.2 mg of protein were incubated in a test tube containing 50 mM sn-glycerol-3-P, 50 mM potassium phosphate (pH 7.0), 1 mM KCN, and 0.2% p-iodonitrotetrazolium violet in a total volume of 0.4 ml for 30 min at 37° C. The incubating mitochondria were continuously agitated during the incubation period by a Dubnoff shaker agitated at 100 cycles/min. Incubation was ceased by the addition of 0.6 ml of 1M acetic acid to the test tube. The iodoformazan formed during the incubation period was extracted into 2 ml of ethyl acetate by adding the ethyl acetate to the test tube, mixing thoroughly, and then decanting the ethyl acetate containing the iodoformazan from the test tube. The optical densities of the iodoformazan containing ethyl acetate layers were read at 490 nm by means of an On Line Instrument Systems, Model 3820 Data System, Spectrophotometry, Cary—15, Version 4 08. An extinction coefficient value of $2.01 \times 10^4/(M\ cm)$ for the iodoformazan product in ethyl acetate was used to calculate enzyme activities.

Cytosolic malic enzyme activity was measured in accordance with the method described in Hsu, R. Y. and Lardy, H. A., *Methods Enzymol.*, vol. 8, pp 230-235 (1967). Briefly, aliquots of the previously prepared cytosol containing 0.1 to 0.5 mg of protein were incubated in a test tube containing 0.8 mM malate, 67 mM triethanolamine buffer (pH 7.4), 4 mM $MnCl_2$, and 0.2 mM NADP in a total volume of 1 ml for 3 min at 26° C. Activity of malic enzyme was calculated from the rate of change in optical density measured at 340 nm from 0.5 to 2 minutes with an On Line Instrument Systems, Model 3820 Data System, Spectrophotometry, Cary—15, Version 4.08.

Results of several tests conducted in accordance with the protocol established above are set forth in Table 1.

TABLE 1

(Enzyme induction in rat liver by $C_{19}$ steriods)

| Steroid | # rats | wt % steroid in diet | G3P-DH (% control[1]) | Malic Enzyme (% control[1]) |
|---|---|---|---|---|
| Δ5 Androstene 3β-ol-17-one (DHEA) | 1 | 0.2 | 380 | 512 |
|  | 29 | 0.1 | 265 | — |
|  | 27 | 0.1 | — | 394 |
|  | 12 | 0.05 | 251 | 337 |
|  | 3 | 0.01 | 139 | 64 |
| Δ5 Androstene 3β,7α-ol-17-one (7α-hydroxy DHEA) | 2 | 0.05 | 292 | 423 |
|  | 2 | 0.033 | 308 | 374 |
| Δ5 Androstene 3β,7α,19-ol-17-one (7α,19-hydroxy DHEA) | 3 | 0.1 | 117 | 118 |
| Δ5-Androstene 3β-ol-17-one (7-keto DHEA) | 3 | 0.1 | 220 | 350 |
|  | 5 | 0.05 | 439 | 449 |
|  | 2 | 0.0575 | 224 | 341 |
|  | 3 | 0.01 | 183 | 229 |
| Δ5-Androstene-3β-ol-7,17-one acetate (7-keto DHEA acetate) | 3 | 0.115 | 261 | 447 |
| Δ5-Androstene-3β-ol-7-methyl-17-one (7-methyl DHEA) | 3 | 0.1 | 91 | 121 |
| Δ5-Androstene 3β,7α,17β-triol | 2 | 0.1 | 227 | 611 |
|  | 2 | 0.01 | 99 | 108 |
| Δ5-Androstene 3β,17β-diol-7-one | 2 | 0.1 | 286 | 1030 |
|  | 3 | 0.05 | 360 | 305 |
|  | 4 | 0.01 | 130 | 175 |
| Δ5-Androstene 3β,17β-diol 7-one diacetate | 3 | 0.13 | 232 | 452 |
|  | 2 | 0.01 | 173 | 119 |

[1] Control activity based upon enzyme activity in the livers of rats fed the stock diet without hormone supplement. In each assay control rats fed only stock diet without hormone supplement were compared with test rats fed stock diet supplement with indicated wt % hormone.

We claim:

1. A method of preventatively treating weight gain which comprises administering to a subject in need of such treatment an effective amount of a steroid selected from the group consisting Δ5-Androstene 3β,7α,17β-triol,
and
Δ5-Androstene 3β,17β-diol-7-one, and derivatives thereof wherein at least one of the hydroxyl groups is esterified with an acid selected from the group consisting of (i) a $C_2$ to $C_{22}$ aliphatic acid, (ii) a $C_{7-12}$ aromatic acid (iii) a $C_3$ or greater dicarboxylic acid in which only one of the carboxyl groups is esterified to the hydroxyl group(s) on the steroid; and (iv) an inorganic acid.

2. The treatment method of claim 1 wherein the step of treating a subject comprises the step of treating a mammal.

3. The treatment method of claim 2 wherein the step of treating a mammal comprises the step of treating a human.

4. The treatment method of claim 1 wherein the step of treating a subject with an effective weight gain preventative amount of a steroid comprises the step of treating the subject with about 0.1 to about 2 grams of the steroid per 100 kg body weight per day.

5. The treatment method of claim 1 wherein the step of treating a subject with an effective weight gain preventative amount of a steroid comprises the step of treating the subject with about 0.5 to 2 grams of the steroid per 100 kg body weight per day.

6. The treatment method of claim 3 wherein the step of treating a human subject with an effective weight gain preventative amount of a steroid comprises the step of treating the human subject with about 0.1 to 2 grams of the steroid per 100 kg body weight per day.

7. The treatment method of claim 4 wherein the step of treating the subject with a weight gain preventative steroid comprises the step of administering a therapeutic dose of the steroid to the subject at least once a week.

8. The treatment method of claim 4 wherein the step of treating the subject with a weight gain preventative steroid comprises the step of administering a therapeutic dose of the steroid to the subject at least once a day.

9. The treatment method of claim 1 wherein the step of treating the subject with a weight gain preventative steroid comprises the step of injecting the subject with the steroid.

10. The treatment method of claim 1 wherein the step of treating the subject with a weight gain preventative steroid comprises the step of ingesting the steroid.

11. A method of treating excessive body fat which comprises administering to an overweight subject an effective amount of a steroid selected from the group consisting of Δ5-Androstene 3β,7α,17β-triol,
and
Δ5-Androstene 3β,17β-diol-7-one, and derivatives thereof wherein at least one of the hydroxyl groups is esterified with an acid selected from the group consisting of (i) a $C_2$ to $C_{22}$ aliphatic acid, (ii) a $C_{7-12}$ aromatic acid (iii) a $C_3$ or greater dicarboxylic acid in which only one of the carboxyl groups is esterified to the hydroxyl group(s) on the steroid; and (iv) an inorganic acid.

12. A method of treating obesity which comprises administering to an obese subject a therapeutic amount of a steroid selected from the group consisting of Δ5-Androstene 3β,7α,17β-triol,
and
Δ5-Androstene 3β,17β-diol-7-one, and derivatives thereof wherein at least one of the hydroxyl groups is esterified with an acid selected from the group consisting of (i) a $C_2$ to $C_{22}$ aliphatic acid, (ii) a $C_{7-12}$ aromatic acid (iii) a $C_3$ or greater dicarboxylic acid in which only one of the carboxyl groups is esterified to the hydroxyl group(s) on the steroid; and (iv) an inorganic acid.

13. A biologically active steroid effective for inhibiting weight gain without inducing a suppression of the appetite or promoting the synthesis of sex hormones comprising Δ5-Androstene 3β,7α,17β-triol and derivatives thereof wherein at least one of the hydroxyl groups is esterified with an acid selected from the group consisting of (i) a $C_2$ to $C_{22}$ aliphatic acid, (ii) a $C_{7-12}$ aromatic acid (iii) a $C_3$ or greater dicarboxylic acid in which only one of the carboxyl groups is esterified to the hydroxyl group(s) on the steroid; and (iv) an inorganic acid.

14. A biologically active steroid effective for inhibiting weight gain without inducing a suppression of the appetite or promoting the synthesis of sex hormones comprising Δ5-Androstene 3β,17β-diol-7-one, and derivatives thereof wherein at least one of the hydroxyl groups is esterified with an acid selected from the group consisting of (i) a $C_2$ to $C_{22}$ aliphatic acid, (ii) a $C_{7-12}$ aromatic acid (iii) a $C_3$ or greater dicarboxylic acid in which only one of the carboxyl groups is esterified to the hydroxyl group(s) on the steroid; and (iv) an inorganic acid.

15. A method of preventatively treating weight gain which comprises administering to a subject in need of such treatment an effective amount of a steroid selected from the group consisting of Δ5-Androstene 3β-ol-7,17-dione
and
Δ5-Androstene 3β,7-diol-17-one and derivatives thereof wherein at least one of the hydroxyl groups is esterified with an acid selected from the group consisting of (i) a $C_2$ to $C_{22}$ aliphatic acid, (ii) a $C_{7-12}$ aromatic acid (iii) a $C_3$ or greater dicarboxylic acid in which only one of the carboxyl groups is esterified to the hydroxyl group(s) on the steroid; and (iv) an inorganic acid.

16. A method of treating excessive body fat which comprises administering to an overweight subject an effective amount of a steroid selected from the group consisting of Δ5-Androstene 3β-ol-7,17-dione
and
Δ5-Androstene 3β,7-diol-17-one and derivatives thereof wherein at least one of the hydroxyl groups is esterified with an acid selected from the group consisting of (i) a $C_2$ to $C_{22}$ aliphatic acid, (ii) a $C_{7-12}$ aromatic acid (iii) a $C_3$ or greater dicarboxylic acid in which only one of the carboxyl groups is esterified to the hydroxyl group(s) on the steroid; and (iv) an inorganic acid.

17. A method of treating obesity which comprises administering to an obese subject a therapeutic amount of a steroid selected from the group consisting of Δ5-Androstene 3β-ol-7,17-dione
and
Δ5-Androstene 3β,7-diol-17-one and derivatives thereof wherein at least one of the hydroxyl groups is esterified with an acid selected from the group consisting of (i) a $C_2$ to $C_{22}$ aliphatic acid, (ii) a $C_{7-12}$ aromatic acid (iii) a $C_3$ or greater dicarboxylic acid in which only one of the carboxyl groups is esterified to the hydroxyl group(s) on the steroid; and (iv) an inorganic acid.

* * * * *

UNITED STATES PATENT AND TRADEMARK OFFICE
CERTIFICATE OF CORRECTION

PATENT NO. : 5,296,481

DATED : March 22, 1994

INVENTOR(S) : Bruce E. Partridge, Lincoln, Nebr.
Henry A. Lardy, Madison, Wis.

It is certified that error appears in the above-identified patent and that said Letters Patent is hereby corrected as shown below:

Column 1, line 53, after "treating a", add --subject with an effective weight gain controlling and/or--

Column 4, line 53, delete "t", add --to--

Column 11, line 4, after "26 C", add --The incubating cytosol was continuously agitated during the incubation period by a Dubnoff shaker agitated at 100 cycles/min.--

Column 11,

TABLE - Under "Steroid" third formula down:

insert "di" after 19- (before hydroxy)

4th formula down, before "17" insert --7,--

Column 11, line 42, after "consisting", add --of--

Signed and Sealed this

Twenty-eight Day of March, 1995

Attest:

BRUCE LEHMAN

Attesting Officer  Commissioner of Patents and Trademarks